(12) United States Patent
Uematsu et al.

(10) Patent No.: US 6,773,901 B2
(45) Date of Patent: Aug. 10, 2004

(54) PCR PRIMERS AND A METHOD FOR DECIDING A BASE SEQUENCE THEREOF REGARDING ADENYLATION

(75) Inventors: Chihiro Uematsu, Kawasaki (JP); Kazunori Okano, Shiki (JP); Takashi Irie, Musashimurayamashi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/083,616

(22) Filed: Feb. 27, 2002

(65) Prior Publication Data

US 2003/0099961 A1 May 29, 2003

(51) Int. Cl.[7] .............................................. C12P 19/34
(52) U.S. Cl. ................................................... 435/91.2
(58) Field of Search ...................... 536/24.33; 435/91.2, 435/6

(56) References Cited

U.S. PATENT DOCUMENTS

| | | | | |
|---|---|---|---|---|
| 5,834,286 A | * | 11/1998 | Nevalainen et al. | 435/196 |
| 6,110,710 A | * | 8/2000 | Smith et al. | 435/91.2 |
| 6,162,900 A | * | 12/2000 | Guerinot et al. | 530/370 |
| 2003/0039976 A1 | * | 2/2003 | Haff | 435/6 |

OTHER PUBLICATIONS

Jakob Stenman, Patrik Finne, Anders Stahls, Reidar Grenman, Ulf–Hakan Stenman, Aarno Palotie and Arto Orpana, "Accurate Determination of Relative Messenger RNA Levels by RT–PCR", Nature Biotechnology, vol. 17, Jul. 1999, pp. 720–722.

Takashi Ito, Keiji Kito, Naoki Adati, Yuko Mitsui, Hisashi Hagiwara, Yoshiyuki Sakaki, "Fluorescent Differential Display: Arbitrarily Primed RT–PCR Fingerprinting on an Automated DNA Sequencer", 1994 Federation of European Biochemical Societies, FEBS Letters 351, pp. 231–236.

Kikuya Kato, "Adapter–Tagged Competitive PCR: a Novel Method for Measuring Relative Gene Expression", Nucleic Acids Research, 1997, vol. 25, No. 22, pp. 4694–4696.

Masato Orita, Hiroyuki Iwahana, Hiroshi Kanazawa, Kenshi Hayashi and Takao Sekiya, "Detection of Polymorphisms of human DNA by Gel Electrophoresis as Single–Strand Conformation Polymorphisms", Proc. Natl. Acad. Sci, vol. 86., Apr. 1989, pp. 2766–2770.

Kokichi Sugano, Yuki Nakashima, Kensei Yamaguchi, Noriko Fukayama, Masato Maekawa, Hisanao Ohkura, Tadao Kakizoe and Takao Sekiya, "Sensitive Detection of Loss of Heterozygosity in the TP53 Gene in Pancreatic Adenocarcinoma by Fluorescence–Based Single–Strand Conformation Polymorphism Analysis Using Blunt–End DNA Fragments" Genes, Chromosomes and Cancer 15 (1996) pp. 157–164.

(List continued on next page.)

*Primary Examiner*—Kenneth R. Horlick
(74) *Attorney, Agent, or Firm*—Reed Smith LLP; Stanley P. Fisher, Esq.; Juan Carlos A. Marquez. Esq.

(57) ABSTRACT

Adenylation of a DNA fragment with a DNA polymerase occurs in the course of PCR, and thus two peaks are detected. To prevent the peak splitting, it is necessary to raise efficiency of adenylation a single peak to occur without changing reaction conditions. To this end, four types of PCR primers which, respectively, have an anchor sequence at 5' terminus so that any of A, C, G or T is attached to at the 5' terminus of the anchor sequence, and PCR is carried out by use of the respective primers to determine efficiencies of adenylation. Subsequently, an anchor sequence that is more likely to undergo adenylation is screened to decide an anchor sequence more likely undergo adenylation, followed by PCR by use of a primer having the decided anchor sequence.

2 Claims, 14 Drawing Sheets

OTHER PUBLICATIONS

Frederic Ginot, Isabelle Bordelais, Simon Nguyen and Gabor Gyapay, "Correction of Some Genotyping Errors In Automated Fluorescent Microsatellite Analysis by Enzymatic Removal of one Base Overhangs", Nucleic Acids Research, 1996, vol. 24, No. 3, pp 540–541.

V.L. Magnuson, D.S. Ally, S.J. Nylund, Z.E. Karanjawala, J.B, Rayman, J.I. Knapp, A.L. Lowe, S. Ghosh and F.S. Collins, "Substrate Nucleotide–Determined Non–Templated Addition of Adenine by Taq DNA Polymerase: Implications for PCR–Based Genotyping and Cloning", BioTechniques, vol. 21, No. 4 (1996), pp. 700–709.

"Modulation of Non–Templated Nucleotide Addition by Taq DNA Polymerase: Primer Modification that Facilitate Genotyping", BioTechniques, Short Technical Reports, vol. 20, No. 6 (1996) pp. 1004–1010.

* cited by examiner

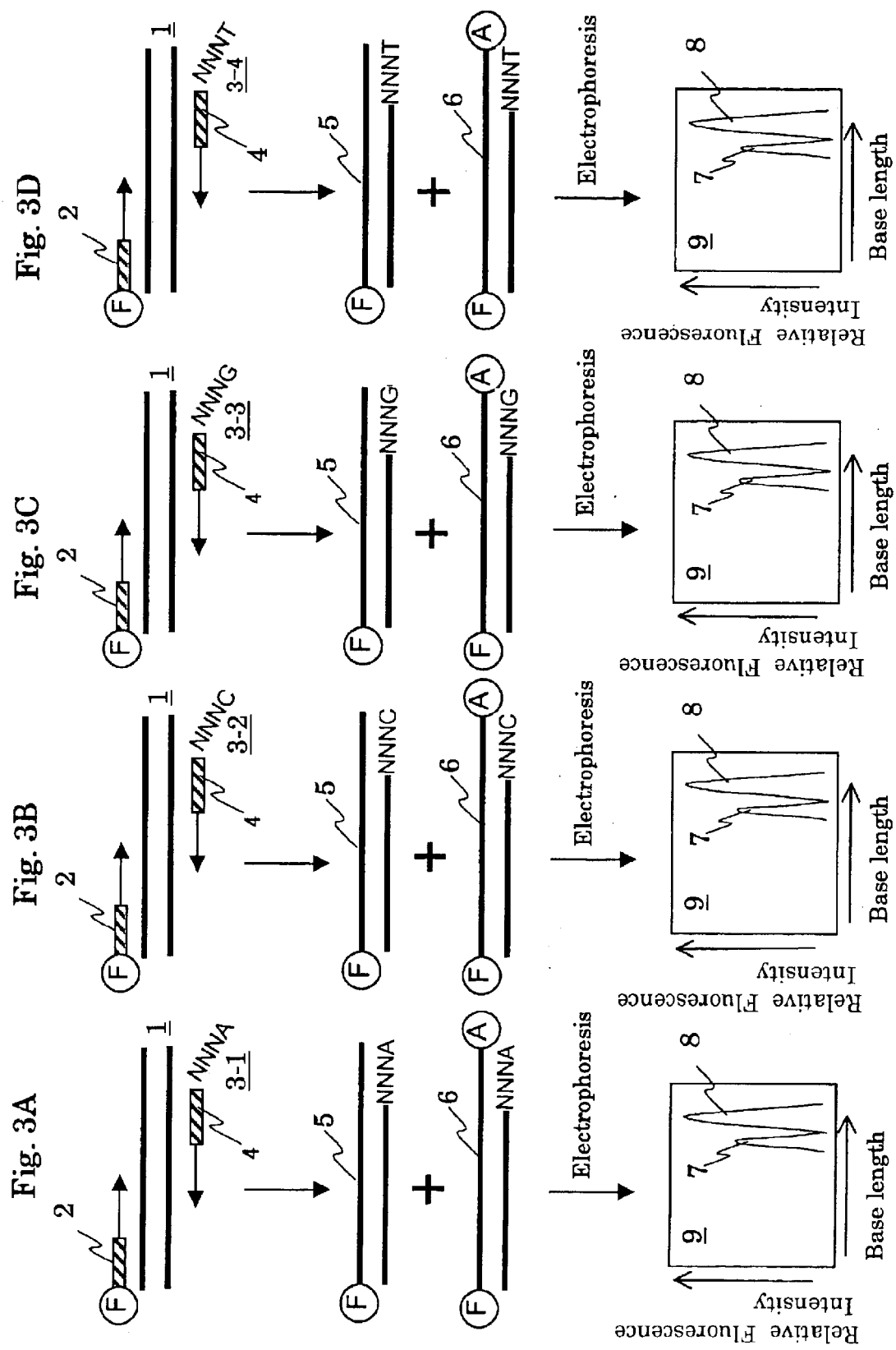

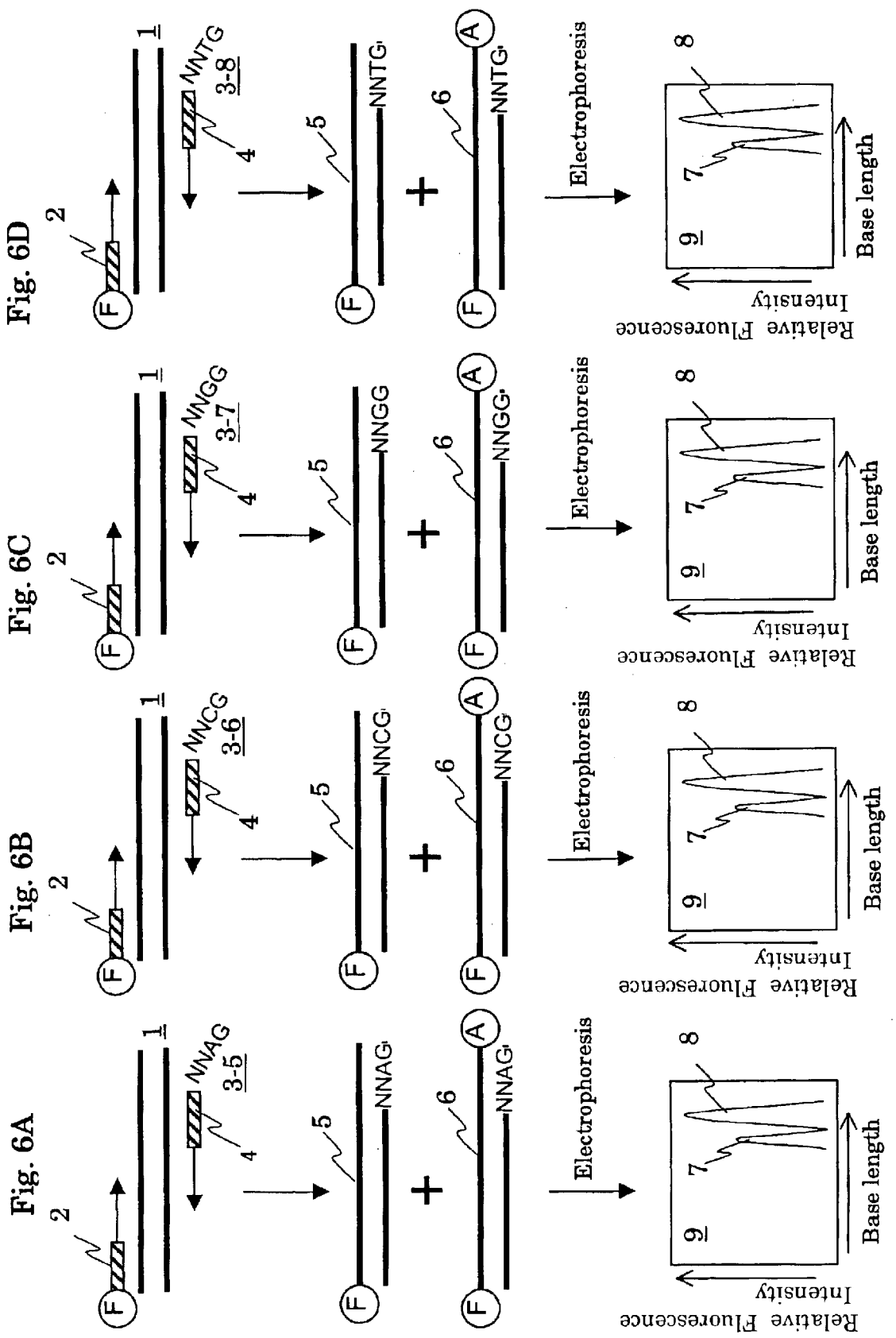

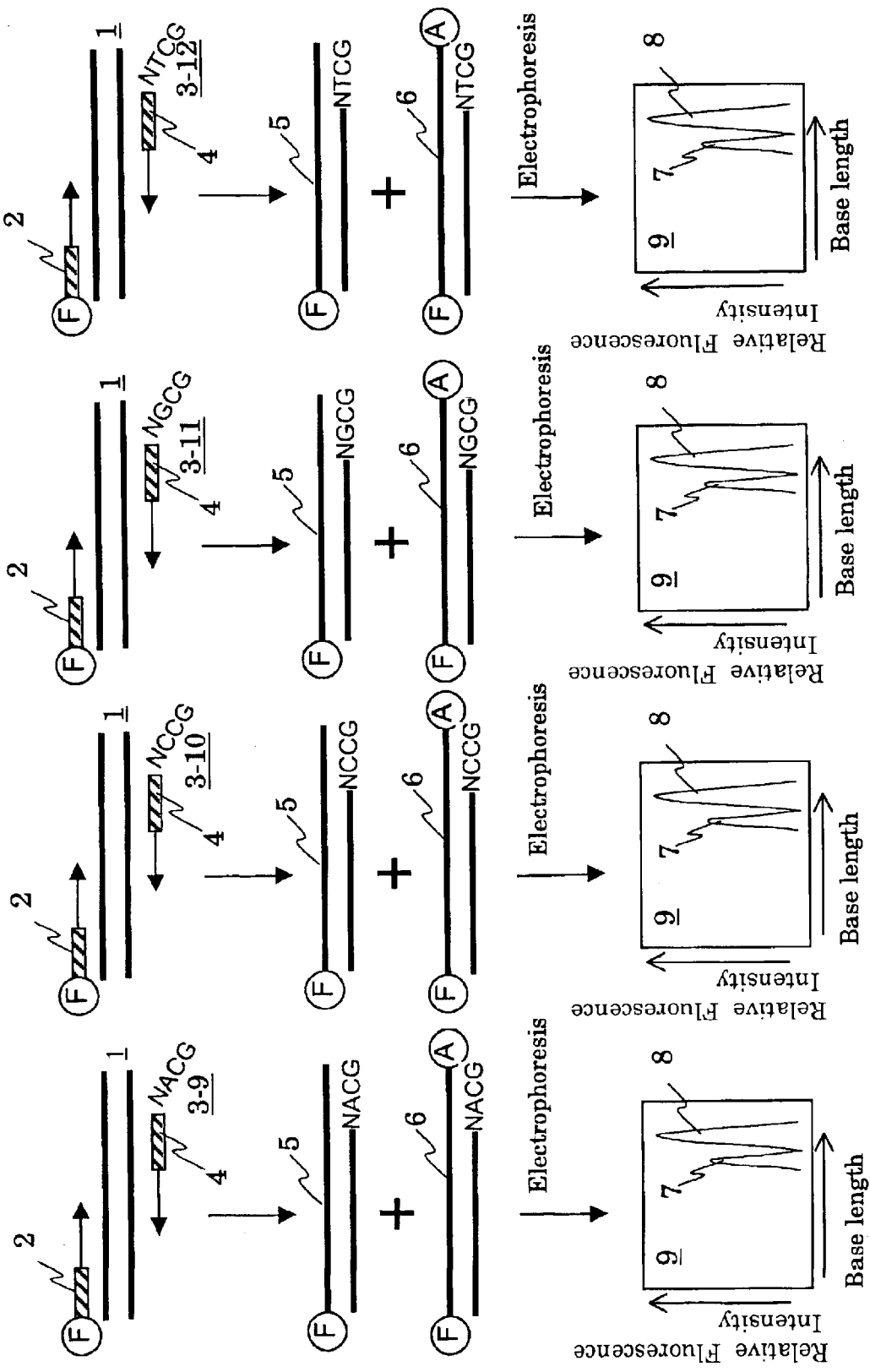

PCR PRIMERS AND A METHOD FOR DECIDING A BASE SEQUENCE THEREOF REGARDING ADENYLATION

BACKGROUND OF THE INVENTION

This invention relates to a primer for PCR and also to a method for deciding a base sequence thereof. More particularly, the invention relates to a PCR primer suitable for the adenylation in the course of PCR using a termostable DNA polymerase having terminal transferase activity and also to a method for deciding the sequence of such a PCR primer.

For the detection of DNA or RNA, it is usual to detect after amplification of a sequence of DNA or RNA obtained from a specimen. For this purpose, PCR amplification is usually performed. In order to detect a PCR-amplified DNA fragment, the DNA fragment is subjected to radioisotopic labeling or is labeled with chemical emission or fluorescence, followed by detection of the labeled DNA fragment after separation of a sample such as by gel electrophoresis. Recently, terminal fluorescence labeling by a synthetic DNA and fluorescence labeling by intercalator capable of intercalation with DNA fragments is enabled and has now been in frequent use. When using an intercalating fluorphore, a DNA fragment subjected to electrophoresis with an agarose gel is labeled with an intercalator, such as ethidium bromide, acridine orange or the like, and detected.

For the measurement of a more accurate fragment length, a terminal fluorescence-labeled DNA fragment is subjected to electrophoresis with a polyacyrlamide gel and detected. For a process requiring the measurement of an accurate fragment length, mention is made of RT-PCR (Reverse Transcriptase-PCR, J. Stenman et al.; "Accurate determination of relative messenger RNA levels by RT-PCR" Nature Biotechnology, 1999, 17, 720–722), FDD (Fluorescent Differential Display, T. Ito et al.; "Fluorescent differential display: arbitrarily primed RT-PCR finger printing on an automated DNA sequencer" FEBS Letters, 1994, 351, 231–236), ATAC-PCR (K. Kato; "Adaptor-tagged competitive-PCR: a novel method for measuring relative gene expression" Nucleic Acids Research, 1997, 25, 4694–4696), SSCP (M. Orita et al.; "Detection of polymorphisms of human DNA by gel electrophoresis as single-Strand conformation polymorphisms" Proc. Natl. Acad. Sci. USA, 1989, 86, 2766–2770) and the like. In these methods, an amplified product is analyzed with a fluorescent-type DNA sequencer after PCR.

SUMMARY OF THE INVENTION

The currently proposed amplification and detection of a DNA fragment based on PCR and electrophoresis has been introduced hereinabove, with many problems undesirably involved in practical applications. More particularly, adenylation to a DNA fragment by the DNA polymerase takes place in the course of PCR, and thus, two peaks are detected based on an adenylated fragment and a non-adenylated fragment, respectively. The probability of the occurrence of the adenylation varies depending on the type of sample DNA and the PCR conditions. This makes it difficult to obtain a peak area of a target DNA fragment due to the splitting of peak.

In SSCP analyses for diagnostic purposes, a peak area is determined for quantitative analysis, enabling one to detect LOH (Loss of Heterozygosity) that will not be judged by a conventional method (K. Sugano et al.; "Sensitive Detection of Loss of Heterozygosity in the TP53 Gene in Pancreatic Adenocarcinoma by Fluorescence-Based Single-Strand Conformation Polymorphism Analysis Using Blunt-End DNA Fragments" Genes, Chomosomes and Cancer, 1996, 15, 157–164, Sensitive Detection of Loss of Heterozygosity in the TP53 Gene in Pancreatic Adenocarcinoma by Fluorescence-Based Singled Strand Conformation Polymorphism Analysis Using Blunt-End DNA Fragments). However, for highly accurate diagnosis, it is necessary to suppress a rate of a peak area of non-adenylated products to peak area of adenylated products to a level within 10%.

To prevent the peak splitting, two procedures are considered including removal of added adenine or positive adenylation caused to occur to 100%. With the method of removal of the added adenine, exnzymatic treatment has to be performed for the removal after PCR (F. Ginot et al.; "Correction of some genotyping errors in automated fluorescent microsatellite analysis by enzymatic removal of one base overhangs" Nucleic Acids Research, 1996, 24, 540–541). On the other hand, in order to cause the adenylation to positively occur, it is necessary to control a concentration of $Mg^{2+}$ ions in a reaction solution and to change reaction conditions. Nevertheless, a difficulty is now involved in stably obtaining an adenylated PCR product. Moreover, although there is a report stating that the efficiency of adenylation changes depending on the sequence in the vicinity of 5' terminus of a template DNA fragment (V. L. Magnuson et al.; "Substrate Nucleotide-Determined Non-Templated Addition of Adenine by Taq DNA Polymerase: Implications for PCR-Based Genotyping and Cloning" Biotechniques, 1996, 21, 700–709), the sequence is not general, with no decision method of the sequence being proposed.

The method of changing the efficiency of adenylation depending on the sequence at 5' terminus of a template DNA is called reverse primer tailing (M. J. Brownstein et al.; "Modulation of Non-Templated Nucleotide Addition by Taq DNA Polymerase: Primer Modifications that Facilitate Genotyping" Biotechniques, 1996, 20, 1004–1010).

An object of the invention is to design, in reverse primer tailing, a sequence that causes adenylation to generally occur in a high efficiency against any type of PCR primer capable of amplifying a target DNA fragment, thereby providing a primer sequence that can amplify a DNA fragment capable of being simply analyzed by electrophoresis.

To achieve the above object, a PCR primer having an anchor sequence wherein a sequence is designed to cause adenylation to occur in a high efficiency at 5' terminus of a reverse primer is used according to the invention. The term "anchor sequence" used herein means a sequence which is positioned at the 5' terminus of a primer sequence that is complementary with a target gene and which is not complementary with a target DNA sequence. The anchor sequence does not hybridize with a target sequence in the first cycle of PCR, but hybridizes only when complementary strand synthesis proceeds at an opposite strand. Accordingly, the anchor sequence hybridizes in the second and subsequent cycles of the PCR, and the resulting amplified fragment becomes one that has a target sequence and an anchor sequence. The anchor sequence can be designed irrespective of a target DNA sequence, so that it is possible to select a sequence capable of causing adenylation to occur in a high efficiency. It is known that the adenylation of PCR is such that the efficiency of adenylation differs depending on the type of base species at the 5' terminus, and the efficiency of the adenylation is decided by approximately 5 bases at the 5' terminus.

In the practice of the invention, four types of primers having anchor sequences wherein only one base at the 5'-terminus among the anchor sequences each made of two to five bases is changed are provided to perform PCR. The results of the PCR are such that the efficiencies of adenylation of the four types of anchor sequences are measured, followed by screening an anchor sequence that is more likely to undergo adenylation. Next, a sequence, in which the adenylation is most likely to occur at the first base of the anchor sequence from the 5' terminus, is decided, followed by synthesis of four types of primers wherein the second base from the 5' terminus of the anchor sequence is changed. Like the case of the first base, PCR is performed and a base species with which adenylation is likely to occur at the sequence of the second base from the 5' terminus is decided. The above procedure is repeated to decide an anchor sequence made of 2 to 5 bases with which adenylation is liable to occur.

PCR is performed using a primer having such an anchor sequence which has been decided by the above procedure and with which adenylation is likely to occur. As a result, an amplified product wherein adenylation has occurred is preferentially obtained. If the ratio of a non-adenylated, amplified product to an adenylated, amplified product is 10% or below, this is usable for diagnosis requiring quantitative analysis.

BRIEF DESCRIPTION OF THE DRAWINGS

FIGS. 3A to 3D are, respectively, flow charts showing the concept of a screening method of anchor sequences that facilitate adenylation according to the invention;

FIGS. 6A to 6D are, respectively, flow charts of deciding a second base from the 5' terminus of each anchor sequence subsequent to FIGS. 3A to 3D;

FIGS. 9A to 9D are, respectively, flow charts of deciding a third base from the 5' terminus of each anchor sequence subsequent to FIGS. 6A to 6D;

FIGS. 13A and 13B, respectively, show an instance of evaluating the influence of adenylation in SSCP wherein FIG. 13A is an electropherogram showing the results of analysis of an amplified product in PCR using an anchor sequence-free reverse primer and FIG. 13B is an electropherogram showing the results of analysis of an amplified product in PCR using a reverse primers having an anchor sequence.

DESCRIPTION OF THE PREFERRED EMBODIMENTS

The invention is described by way of examples.

EXAMPLE 1

Figure 1:
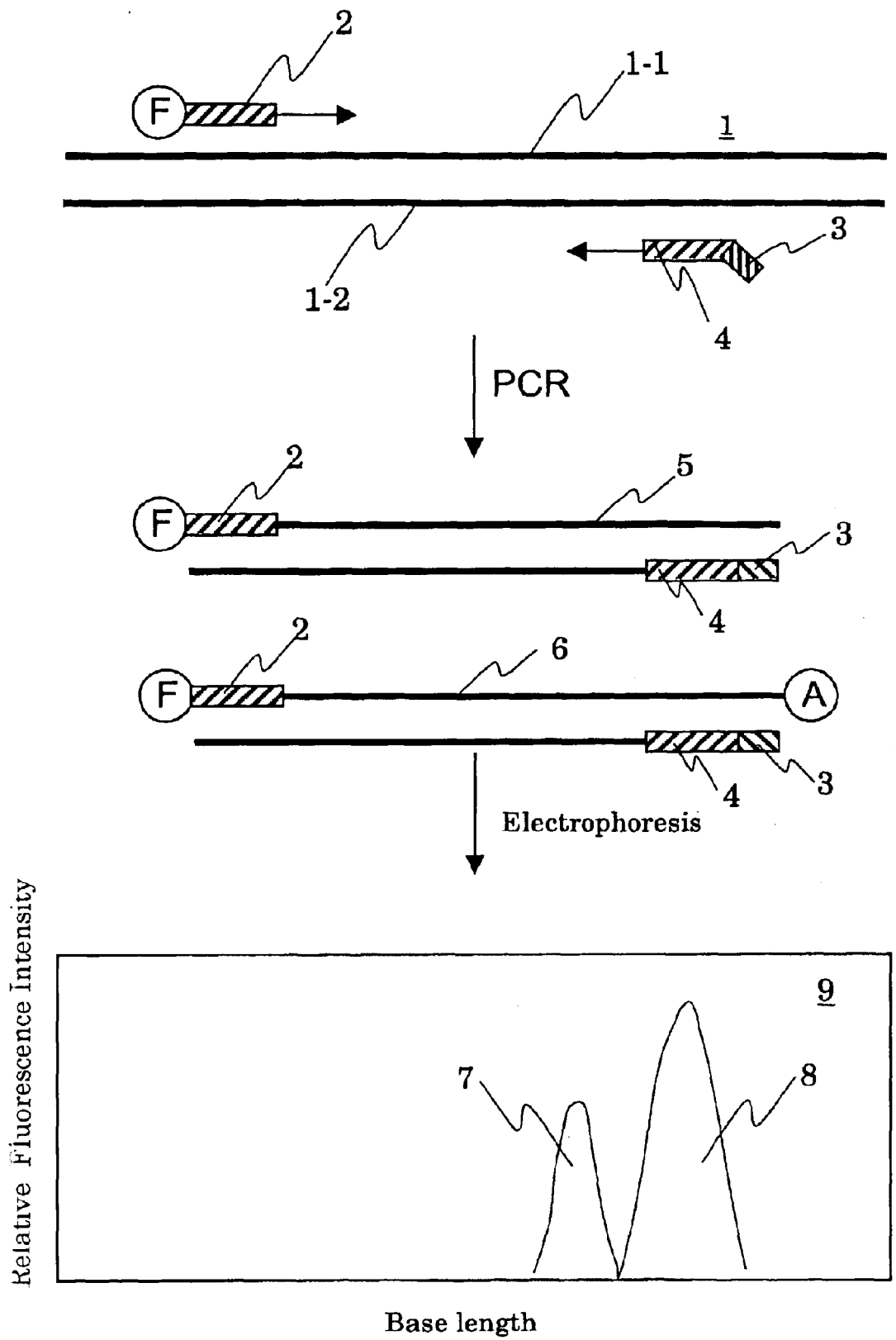
FIG. 1 is a schematic view showing PCR using a PCR primer having an anchor sequence according to the invention, an embodiment of the resulting product, and the evaluation of the PCR primer having an anchor sequence with a labeled fluorescence intensity after electrophoresis of the product.

FIG. 1 is a schematic view showing PCR using a PCR primer having an anchor sequence according to the invention, an embodiment of the resulting product, and the evaluation of the PCR primer having an anchor sequence with a labeled fluorescence intensity after electrophoresis of the product. Reference numeral 1 indicates sample DNA. Reference numeral 2 indicates a forward primer for PCR and reference numeral 4 indicates a reverse primer for PCR. When the sample DNA 1 is denatured into two single strands 1-1 and 1-2, the respective primers, respectively, have a base length of 12 to 20 bases which are complementary to two single strands. The forward primer 2 is labeled with a fluorphore F at the 5' terminus thereof. The anchor sequence 3 is connected at the 5' terminus of the reverse primer 4. It will be noted that the anchor sequence 3 has a base length of 2 to 5 bases and is one which is not complementary to the target DNA sequence. Accordingly, the base length of the reverse primer 4 containing the anchor sequence 3 corresponds to 14 to 25 bases.

Such primers as set out above are provided, and when PCR is performed using a thermostable DNA polymerase having terminal transferase activity, the primers 2, 4 are, respectively, elongated as shown by arrows. As stated hereinbefore, in the second and subsequent cycles of PCR, an amplified fragment becomes one that has a target sequence and an anchor sequence, and this fragment serves as target DNA, thereby permitting the elongation reaction of the forward primer 2 to occur. At this stage, there are amplified a fragment 5, which has not undergone adenylation at the 3' terminus of the resulting PCR product, and a fragment 6, which has undergone adenylation at the 3' terminus. The added adenine is indicated as A enclosed with a circle in the figure.

The thus obtained PCR product is analyzed by electrophoresis, revealing that as shown in electropherogram 9, a peak 8 derived from the adenylated fragment 6 and a peak 7 derived from the non-adenylated fragment 5 are detected. In the electropherogram, the horizontal axis indicates a base length wherein the base lengths of the peak 8 and the peak 7 differ only by one base of adenine resulting from the absence or presence of added adenine. For better understanding of the figure, the respective peaks are shown as kept away from each other.

If the 5' terminus of the anchor sequence 3 is converted to a base that facilitates the adenylation, it becomes possible that the peak 8 derived from the adenylated fragment 6 is made significantly greater than the peak 7 derived from the non-adenylated fragment 5, thus improving the accuracy of the analysis.

In Example 1, cDNA was prepared from RNA extracted from a wild strain of budding yeast and used as sample DNA1. As PCR forward primer 2, a primer for forward PCR that has (sequence 1) and is labeled with fluorphore HEX at the 5' terminus thereof was used.

Sequence 1

5'-HEX-agaaagagggc tccaatttct c-3'

On the other hand, a PCR primer having (sequence 2) at a moiety that is complementary relative to the sample DNA was used among the PCR reverse primers 4.

Sequence 2

5'-gtgagcaata cacaaaattg ta-3'

When PCR of the sample DNA1 derived from the wild strain of germinated yeast was carried out by use of the above primer pair, a PCR product having a length of 187 bp is amplified. PCR was performed such that using Ex-Taq polymerase (Takarashuzo K. K.), 25 cycles, each consisting of 94° C. and 30 seconds, 60° C. and 60 seconds and 72° C. and 30 seconds, were repeated, followed by keeping the conditions of 72° C. and 2 minutes. The resulting PCR product was subjected to electrophoretic analysis using a 3.5% polyacrylamide gel. The resultant electrophoretic data were corrected with respect to the base line according to a software attached to the electrophoresis device used, thereby making an electropherogram.

Figure 2A:
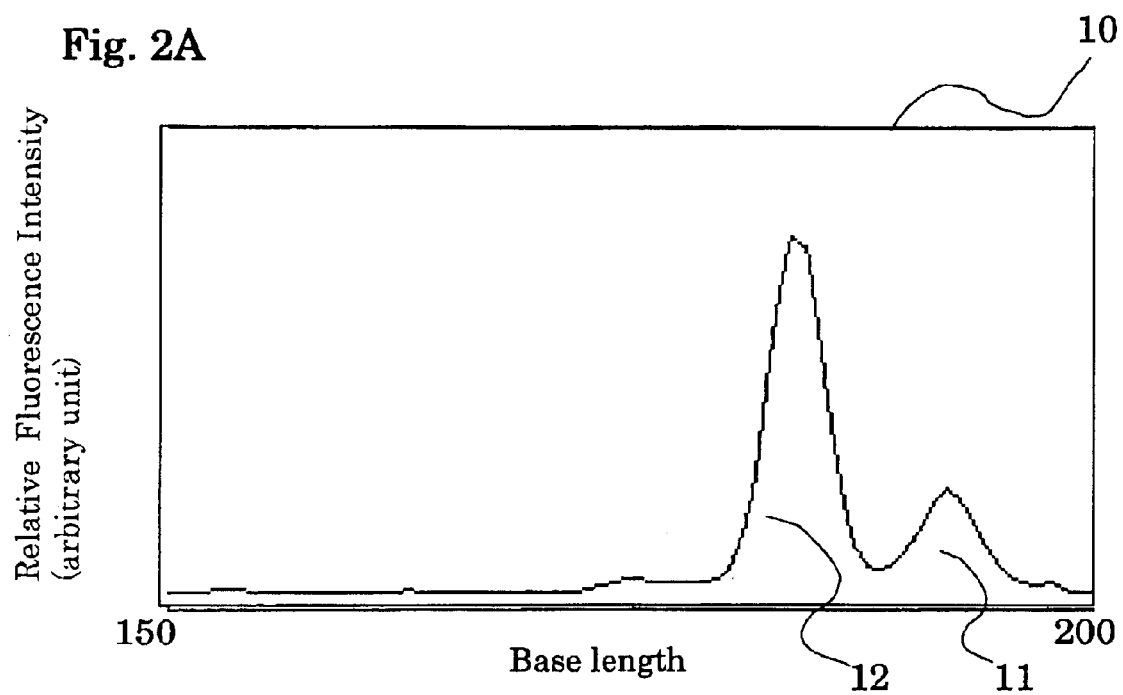
FIG. 2A is an electropherogram of an amplified product in PCR using an anchor sequence-free reverse primer.
Figure 2B:
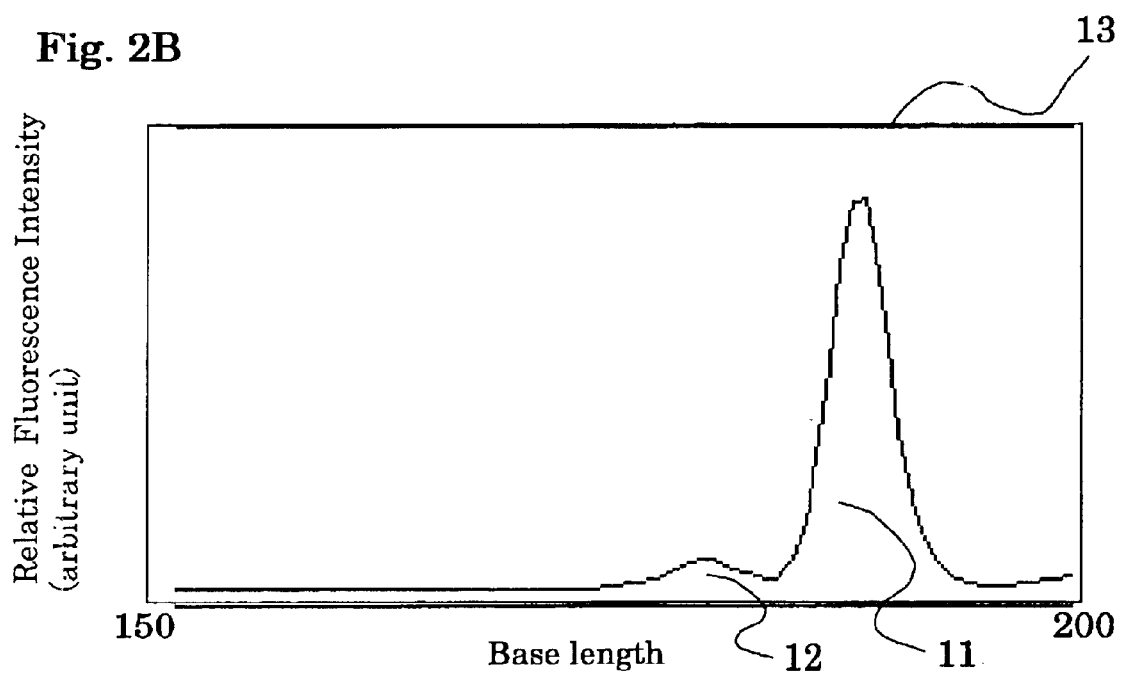
FIG. 2B is an electropherogram of an amplified product in PCR using a reverse primers having an anchor sequence.
Figure 4A:
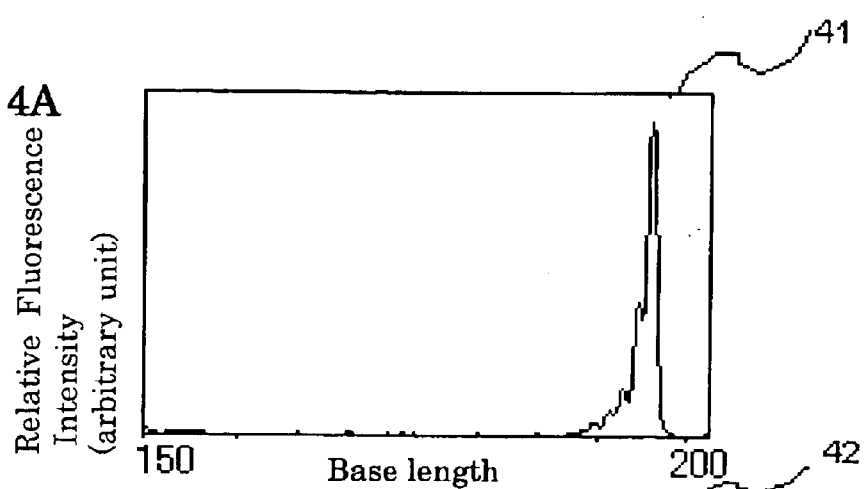
FIGS. 4A to 4D are, respectively, electropherograms particularly showing the results of electrophoresis of PCR products obtained by using PCR reverse primers having four types of anchor sequences.
Figure 4B:
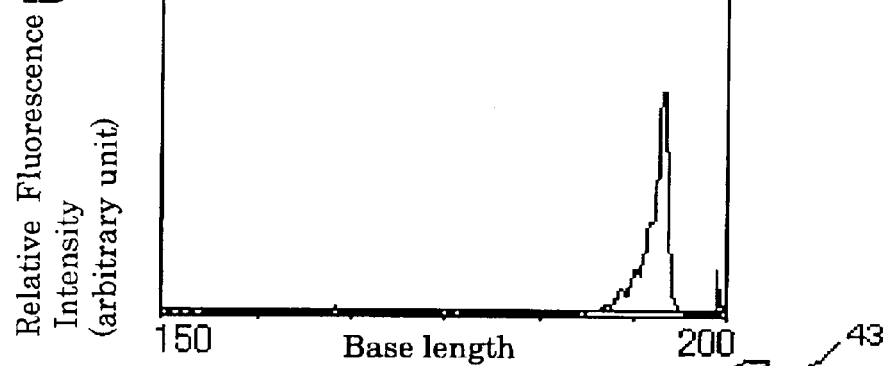
Figure 4C:
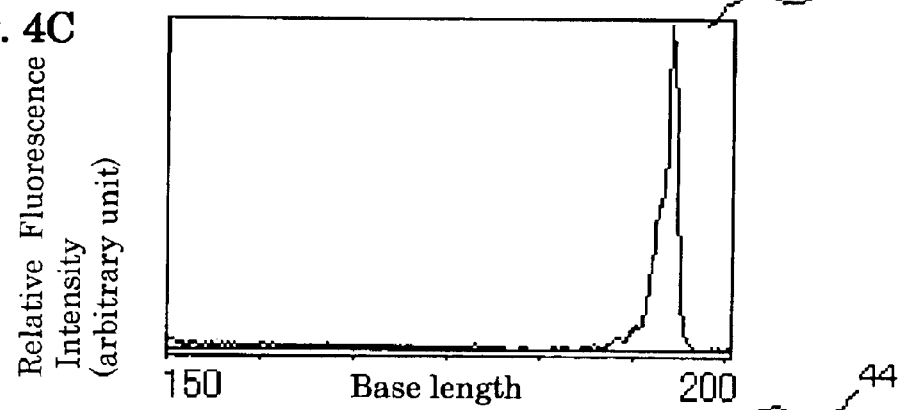
Figure 4D:
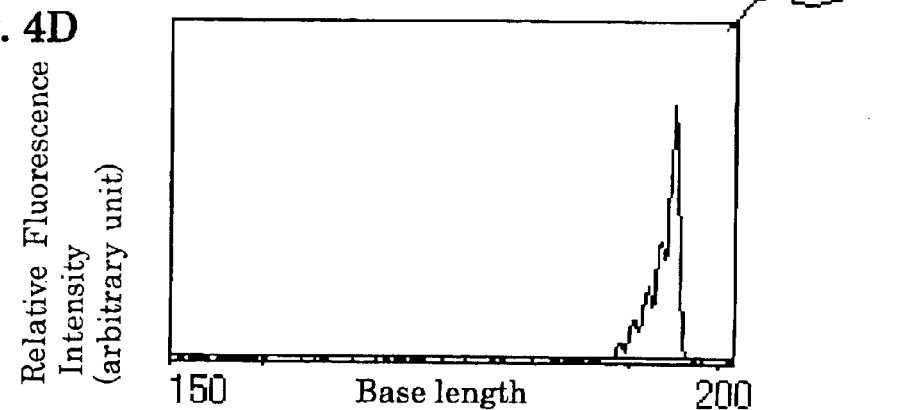

FIG. 2A is an electropherogram 10 of an amplified product in PCR using an anchor sequence-free reverse primer, and FIG. 2B is an electropherogram 13 showing an amplified product in PCR using a reverse primer having an anchor sequence. With the electropherogram of FIG. 2A, as will be apparent from the comparison between the peak 11 of the adenylated fragment 6 and the peak 12 of the non-adenylated fragment 5, the peak 11 is smaller than the peak 12. The ratio of the peaks is approximately at 1:4. On the other hand, with the electropherogram 13 of FIG. 2B, the comparison between the peak 11 of the adenylated fragment 6 and the peak 12 of the non-adenylated fragment 5 reveals that the peak 11 is predominantly greater than the peak 12. More particularly, it will be seen that in the PCR of this example, while adenylation is promoted by the reverse primer having the anchor sequence, the non-adenylated fragment 5 is suppressed to a level of 10% or below of the adenylated fragment 6.

FIGS. 3A to 3D are, respectively, a flow chart showing the concept of a screening method of anchor sequences that facilitate adenylation according to the invention. As illustrated with respect to FIG. 1, there are provided sample DNA1, and PCR forward primer 2 and PCR reverse primer 4, both for carrying out PCR using DNA 1, converted to single strands, as templates, respectively. In order to amplify a target DNA fragment, the PCR forward primer 2 has such a sequence as to be complementary to a target sequence and is labeled with fluorphore F. The PCR reverse primer 4 is composed of a sequence 4 complementary to a target sequence and anchor sequences 3-1, 3-2, 3-3 or 3-4, which are not complementary to the target sequence and are made of four bases.

Attention should be paid to the 5' terminii of the anchor sequences 3-1, 3-2, 3-3 and 3-4, from which it will be apparent that four types of bases such as A, C, G and T are, respectively, at 5' terminus. It is to be noted that the base sequence of NNN means 64 (=4×4×4) base sequences consisting of all combinations of A, C, G and T. The sequences 3-1, 3-2, 3-3 and 3-4 are mixtures of 64 oligonucletides, and, in practice, can be handled as four types of oligonucletides made of A, C, G and T bases at the 5' terminus. In FIG. 3A, PCR is performed, like FIG. 1, by means of a PCR reverse primer wherein A is attached to at the 5' terminus of the anchor sequence 3-1. As a result, a non-adenylated DNA fragment 5 and an adenylated DNA fragment 6 are obtained. Thus, as shown in electropherogram 9, the area of a peak 7 derived from the non-adenylated, amplified DNA fragment 5, and the area of a peak 8 derived from the adenylated, amplified DNA fragment 6 can be discriminated from each other and detected. One of 64 oligonucletides may have such a sequence as to be complementary to the target DNA fragment, and the other 63 oligonucletides are non-complementary, so that it may be possible to substantially deal with these oligonucletides as a non-complementary anchor sequence. Hence, the peak area of peak 7 and 8 are calculated as an oligonucletide that has an anchor sequence having base A at the terminus thereof. Likewise, in FIGS. 3B to 3D, the area of the peak 7 derived from the non-adenylated, amplified DNA fragment 5 and the area of the peak 8 derived from the adenylated, amplified DNA fragment 6 can be discriminated from each other and detected.

The area S of the peak 7 derived from the non-adenylated, amplified DNA fragment 5 and the area $S_A$ of the peak 8 derived from the adenylated, amplified DNA fragment 6 are obtained, and the efficiency of adenylation of ($S_A/(S_A+S)$) is calculated from the ratio between the peak areas. The base at the 5' terminus of the PCR reverse primer, which gives the highest efficiency of adenylation is adopted as an anchor sequence.

Figure 5:
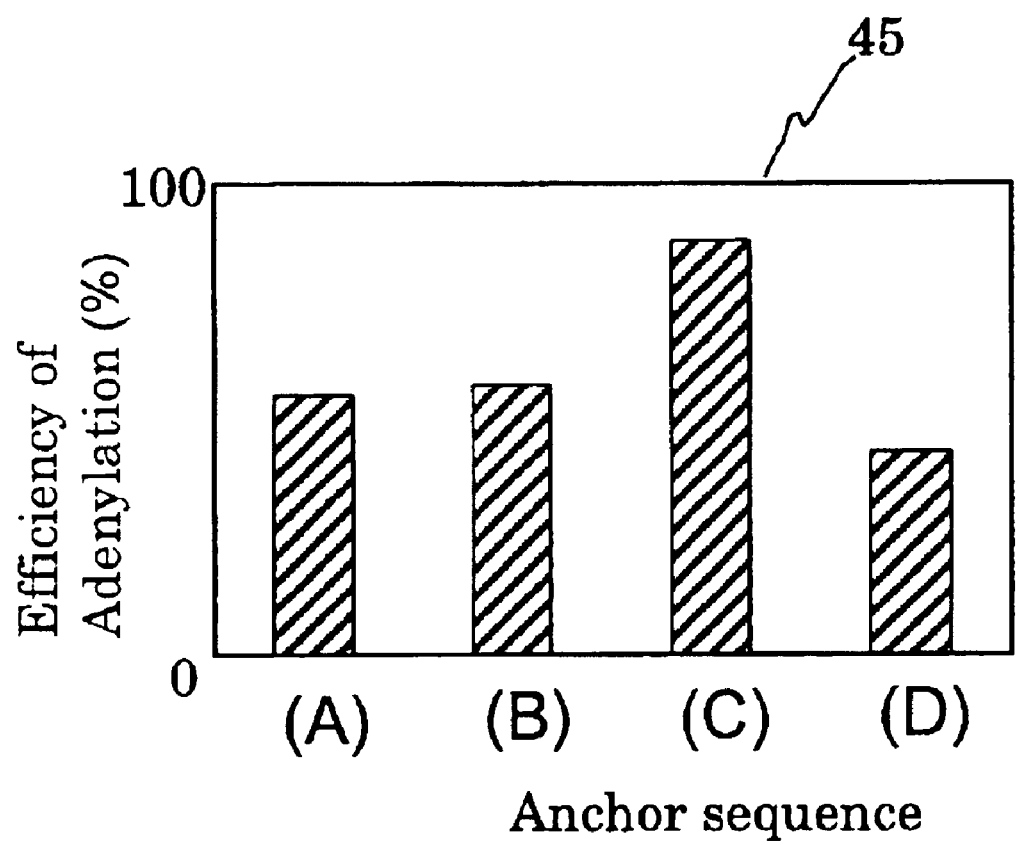
FIG. 5 is a graph showing, for comparison, the results of the efficiency of adenylation of $(S_A/(S_A+S))$ based on the results of electrophoresis of the PCR products obtained by using PCR reverse primers having four types of anchor sequences.

In FIGS. 4A to 4D, specific examples of the results of electrophoresis of PCR products obtained by using PCR reverse primers having four anchor sequences 3-1, 3-2, 3-3 and 3-4 are shown as electropherograms 41, 42, 43 and 44, respectively. From each electropherogram, the area $S_A$ of a peak derived from the adenylated, amplified DNA fragment 6 and the area S of a peak derived from the non-adenylated, amplified DNA fragment 5 are decided, from which the adenylation efficiency of ($S_A/(S_A+S)$) is calculated for the respective primer reverse primers, with the results shown in FIG. 5 as graph 45 for comparison. In the graph, the anchor sequence (c) yields the highest adenylation efficiency and this sequence was selected. The anchor sequence (c) had base G, so that G was adopted as a base at the 5' terminus of the anchor sequence.

As stated hereinabove, anchor primers wherein four types of bases were used as a base at the 5' terminus of the anchor sequence were used, of which an anchor sequence exhibiting the best effect was firstly selected. Secondly, while using the thus selected base at the 5' terminus of the anchor sequence, anchor primers wherein four types of bases are applied to as a base at the second from the 5' terminus are used, and an anchor sequence having the best effect is selected from among the four anchor sequences. When the above procedure is repeated for screening, for example, the bases of all the anchor sequences 3 made of four bases can be decided.

FIGS. 6A to 6D show flow charts of deciding the second base from the 5' terminal of the anchor sequences subsequent to FIGS. 3A to 3D. Initially, PCR reverse primers having anchor sequences 3-5, 3-6, 3-7 and 3-8 wherein the base at the 5' terminus is decided as G are provided. N in the base sequences of the anchor sequences 3-5, 3-6, 3-7 and 3-8 of the PCR reverse primers consists of a mixed base of A, C, G and T. Accordingly, the base sequences of NN of the anchor sequences 3-5, 3-6, 3-7 and 3-8 of the PCR reverse primers in FIGS. 6A to 6D are made of 16 (4×4) base sequences composed of all the combinations of A, C, G and T. The target DNA is amplified by the combinations of the PCR reverse primers having the four anchor sequences 3-5, 3-6, 3-7 and 3-8 and the fluorescence-labeled PCR forward primer 2. The thus amplified DNA fragments are each analyzed by gel electrophoresis, from which the peak areas of the non-adenylated DNA fragment 5 and the adenylated DNA fragment 6 are decided, of which an anchor sequence having the best effect is selected as second base species from the 5' terminus.

In FIGS. 7A to 7D, the specific examples of the results of electrophoresis of the PCR products obtained by use of the PCR reverse primers having the four anchor sequences 3-5, 3-6, 3-7 and 3-8 are shown as electropherograms 80, 81, 82 and 83, respectively. The peak area $S_A$ derived from the adenylated, amplified DNA fragment 6 and the peak area S derived from the non-adenylated, amplified DNA fragment 5 are, respectively, decided from each electropherogram, and the adenylation efficiency of ($S_A/(S_A+S)$) is calculated for the respective primer reverse primers, with the results shown in FIG. 8 as graph 84 for comparison. From the FIG. 8, it will be seen that the anchor sequence (c) gives the best efficiency of adenylation and thus, this sequence (c) is selected. Since the anchor sequence (c) has base G, G is adopted as a second base from the 5' terminus of the anchor sequence. More particularly, evidence is given that the bases up to the second from the 5' terminus of the anchor sequence should favorably be GG.

Figure 7A:
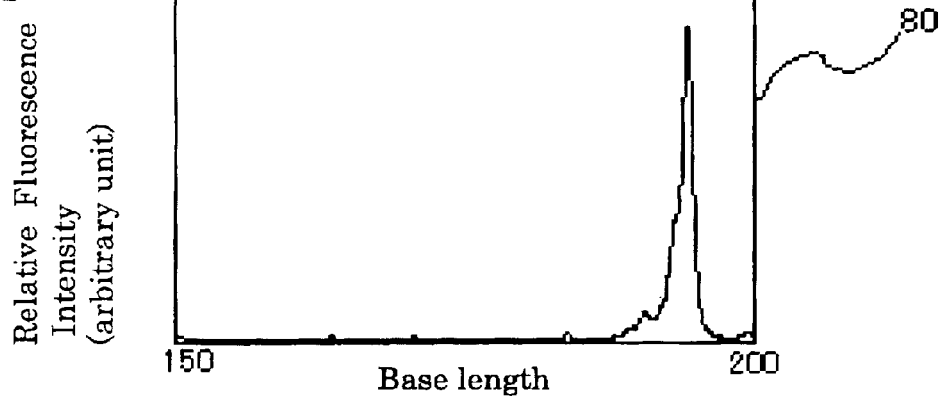
FIGS. 7A to 7D are, respectively, electropherograms showing the results of electrophoresis of PCR products obtained by using PCR reverse primers having four types of anchor sequences.
Figure 7B:
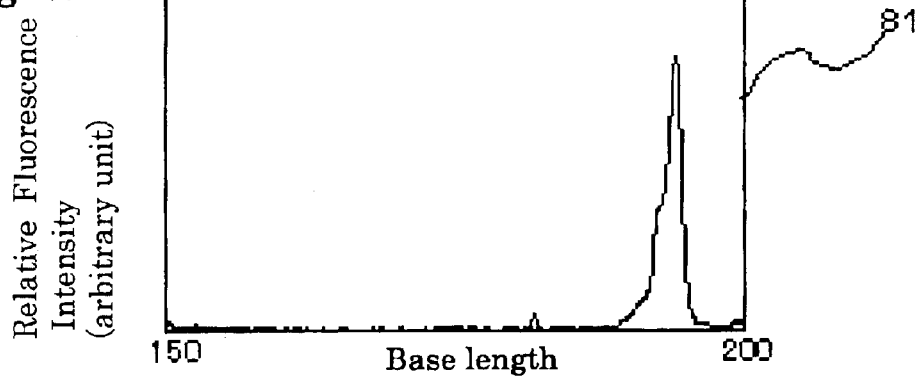
Figure 7C:
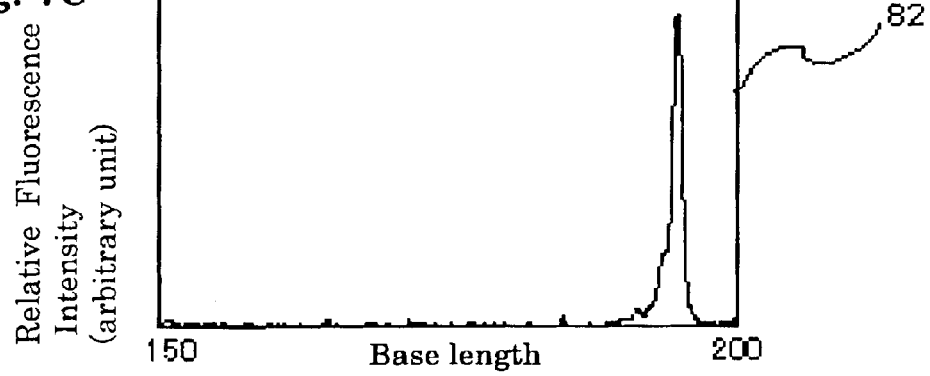
Figure 7D:
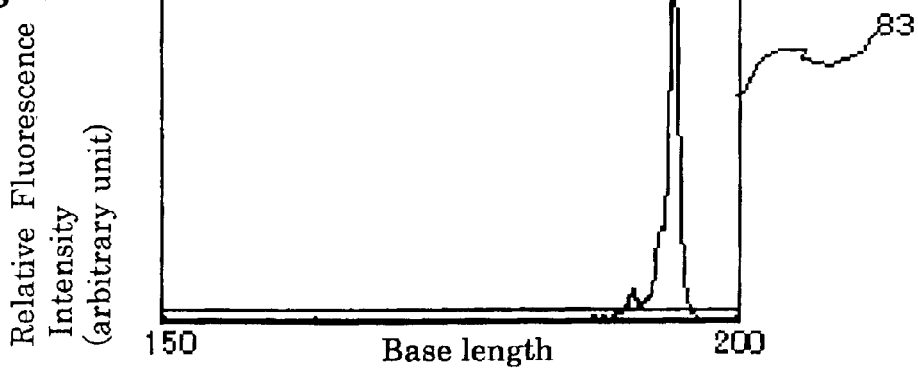
Figure 8:
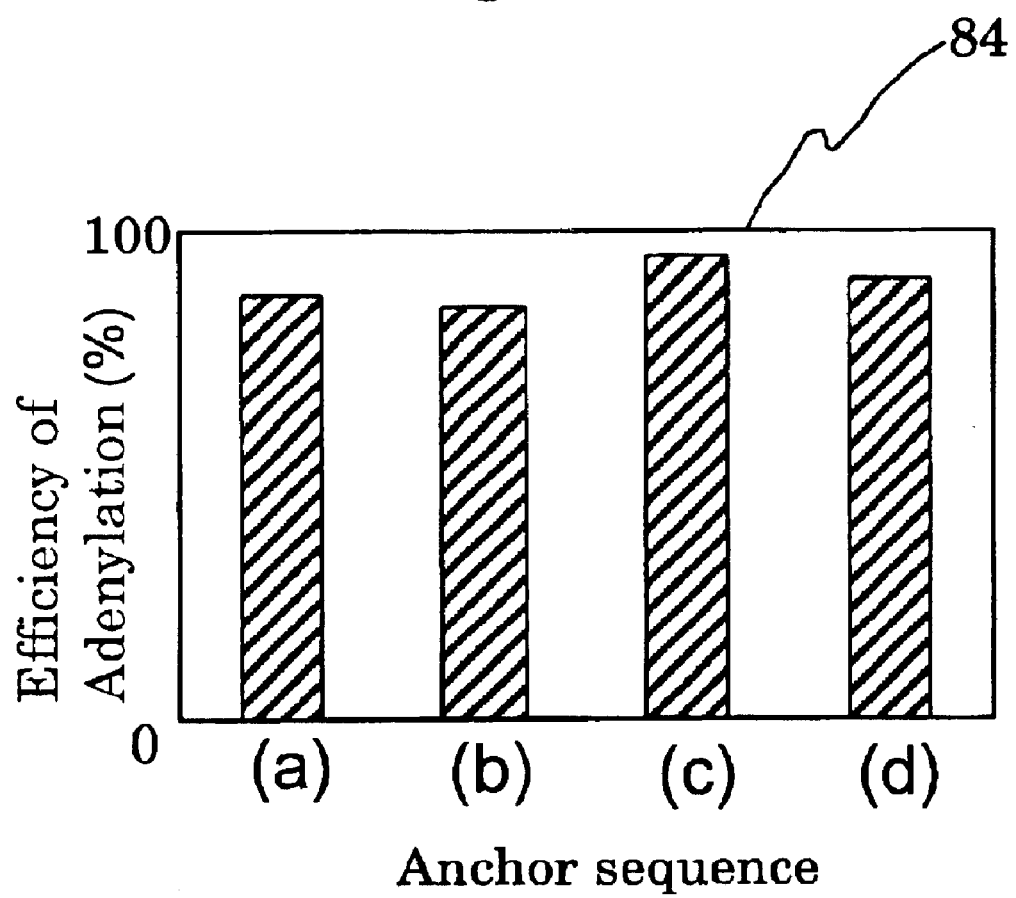
FIG. 8 is a graph showing, for comparison, the results of the efficiency of adenylation of $(S_A/(S_A+S))$ based on the results of electrophoresis of the PCR products obtained by using PCR reverse primers having four types of anchor sequences.
Figure 10A:
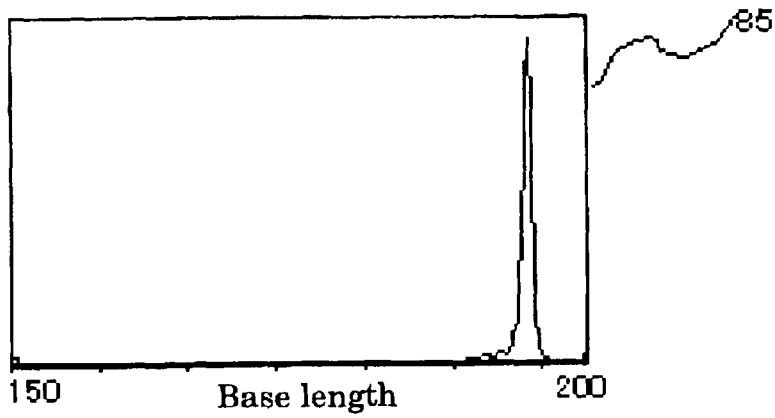
FIGS. 10A to 10D are, respectively, electropherograms obtained by electrophoresis of amplified products wherein PCR is carried out by use of PCR reverse primers having four types of anchor sequences.
Figure 10B:
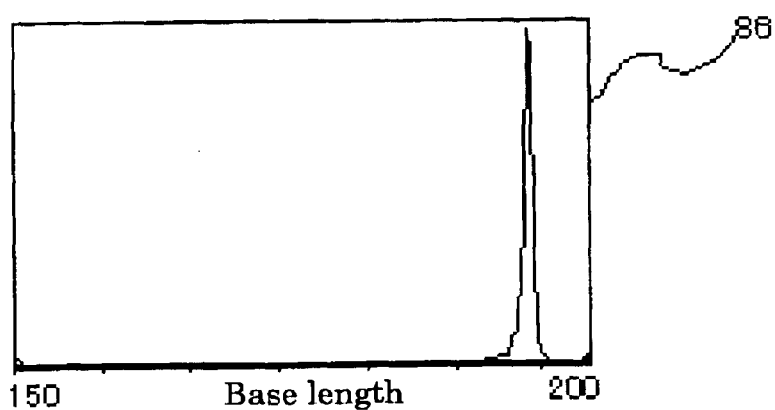
Figure 10C:
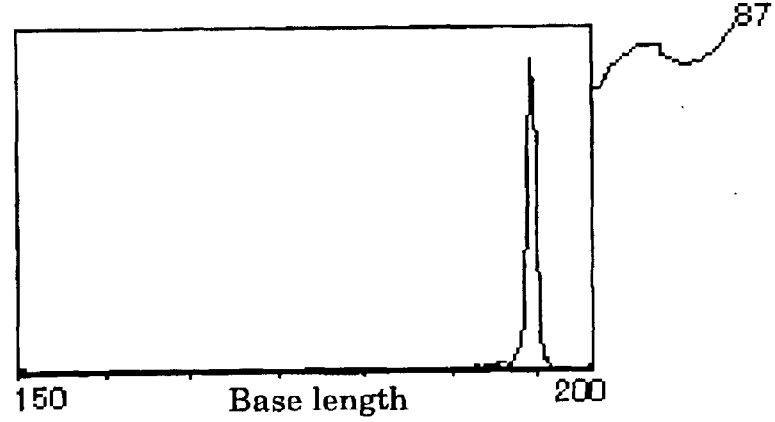
Figure 10D:
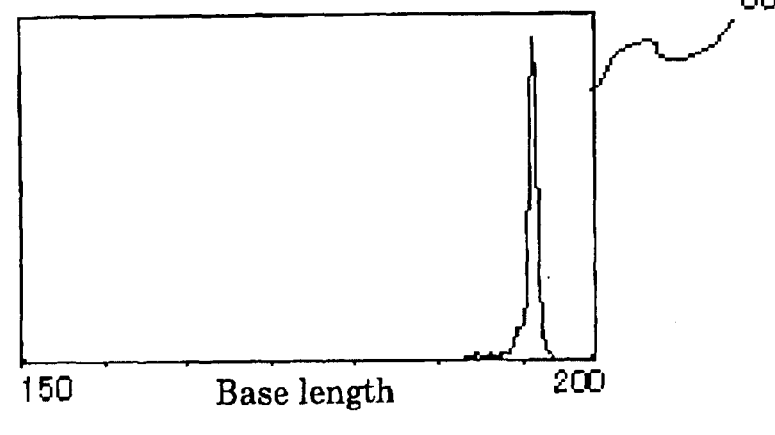

It will be noted that in FIG. 8, the anchor sequences (a) and (d) other than the anchor sequence (b) whose effect is lowest were also checked, with the following results being obtained. The efficiencies of adenylation of both (a) and (d) in FIG. 8 are substantially equal to that of (c) in FIG. 8. (d) was not adopted because in the electropherogram 83 shown in FIG. 7D, the peak derived from the non-adenylated, amplified product 5 and the peak derived from the adenylated, amplified product 6 were detected as being separate from each. With respect to (a), the peak of electropherogram 80 shown in FIG. 7A is such that the peak derived from the non-adenylated, amplified product 5 and the peak derived from the adenylated, amplified product 6 are recognized as the same as one peak and this sequence was adopted. The base of the anchor sequence (a) is A, which was adopted as the second base from the 5' terminus of the anchor sequence. That is, it is shown that the bases up to the second base from the 5' terminus of the anchor sequence should favorably be GA.

As a result, it is shown in this example that the anchor sequence is favorably such that the bases up the second from the 5' terminus may be GG or GA.

In FIGS. 9A to 9D, there are shown flow charts showing the decision of a third base from the 5' terminus subsequent to FIGS. 6A to 6D. In this instance, the case where the bases up to the second from the 5' terminus of the anchor sequence are decided as GG is described, and if GA is adopted, it is sufficient to read GG for GA. Initially, PCR reverse primers having anchor sequences 3-9, 3-10, 3-11 and 3-12 which individually have two bases of GG from the 5' terminus are provided. N in the base sequences of the anchor sequences 3-9, 3-10, 3-11 and 3-12 of the PCR reverse primers consists of a base sequence of four bases of A, C, G and T. Accordingly, PCR reverse primers having anchor sequences 3-9, 3-10, 3-11 and 3-12 and the base sequence of N are four types of bases of A, C, G and T. The target DNA is amplified by PCR through combinations of the PCR reverse primers having the thus provided four anchor sequences 3-9, 3-10, 3-11 and 3-12 and a fluorescence-labeled PCR forward primer 2. The amplified DNA fragment is analyzed by gel electrophoresis, and the peak areas of the non-adenylated DNA fragment 5 and the adenylated DNA fragment 6, from which an anchor sequence having the best effect is selected as third base species from the 5' terminus.

FIGS. 10A to 10D, respectively, show electropherograms obtained by electrophoresis of amplified products, which are obtained by PCR using the PCR reverse primers having the four anchor sequences 3-9, 3-10, 3-11 and 3-12. The adenylation efficiency of each PCR reverse primer is obtained from the respective electropherograms.

Figure 11:
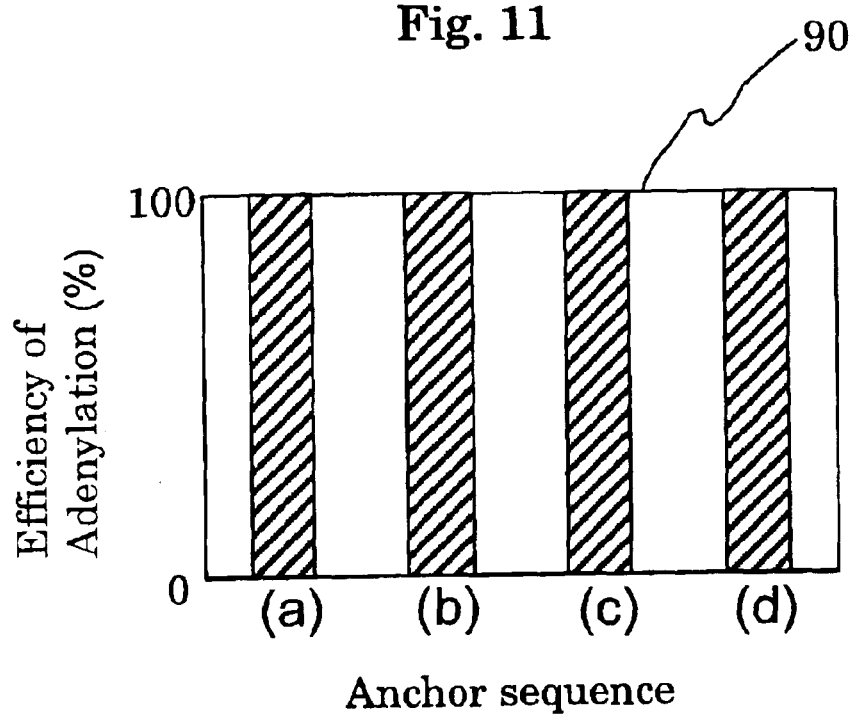
FIG. 11 is a graph showing, for comparison, the efficiency of adenylation of the amplified products wherein PCR is carried out by using PCR reverse primers having four types of anchor sequences.

FIG. 11 is a graph 90 showing, for comparison, the adenylation efficiencies of the amplified products subjected to PCR by use of PCR reverse primers having four anchor sequences 3-9, 3-10, 3-11 and 3-12. Like the foregoing instances, an anchor having the best effect is selected as a base species at the third base from the 5' terminus. With Example 1, the results of the screening for the third base reveal that no significant difference is found in the efficiency of adenylation and that only adenylated fragments were detected for all the PCR reverse primers having such anchor sequences as mentioned above. Accordingly, the selection of the third base is unnecessary.

In this way, an anchor sequence which enables the efficiency of adenylation to be set at a required value by proper selection of bases of up to the second from the 5' terminus is decided in this example. Accordingly, it is not always necessary that the anchor sequence be composed of 4 bases. More particularly, it will be seen that the anchor sequence of Example 1 may be one which has a GA or GG sequence at the 5' terminus. In general, when screening is effect for five or more bases, the difference in the efficiency of adenylation becomes small. In this sense, it is sufficient for practical applications that the length of an anchor sequence corresponds to approximately 5 bases.

Figure 12A:
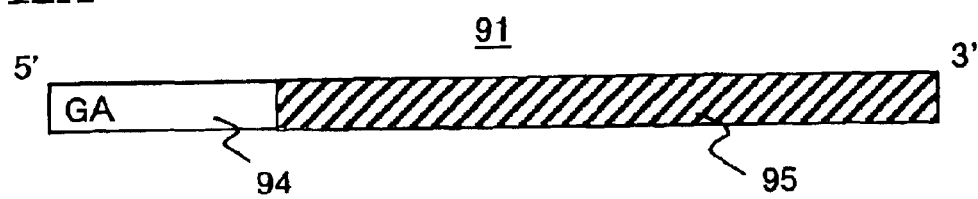
FIGS. 12A and 12B are, respectively, a schematic view showing a PCR reverse primer structure having an anchor sequence decided in the example of the invention.
Figure 12B:
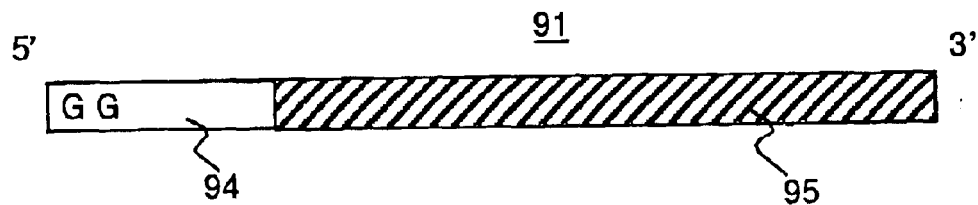

FIGS. 12A and 12B schematically show PCR reverse primer structures having such anchor sequences as decided in this example, respectively. A PCR reverse primer 91 having the anchor sequence is constituted of a sequence part 95 hybridized with target DNA and a anchor sequence 94 which is adjacent to the 5' terminus of the sequence 95 and is non-complementary to the target DNA. The two bases at the 5' terminus of the anchor sequence is in a GA base sequence or GG base sequence.

When the anchor sequence is made of three bases, the anchor sequences are possible at 4×4=64 in total. In Example 1, an anchor sequence that ensures a high efficiency of adenylation can be decided by three cycles of screening among 64 sequences. The base sequence of the PCR reverse primer is, in turn, decided such that the thus decided anchor sequence is positioned at the 5' terminus of a sequence that is complementary to the target DNA. PCR using the primer having such an anchor sequence as to ensure a high efficiency of adenylation as in this example is carried out, and according to an analytical method of detecting an amplified product by electrophoresis, only the peak of an adenylated, amplified product can be detected, thereby obtaining the results of analysis of high resolution.

EXAMPLE 2

The method of the invention is applicable to SSCP. In the same manner as illustrated with reference to FIGS. 3A–3D to 11, target DNA is subjected to PCR amplification using a PCR forward primer labeled with flurophore and PCR reverse primer having an anchor sequence wherein a combination of bases capable of causing a high efficiency of adenylation are arranged at the 5' terminus. As a result of the PCR, an adenylated fragment and a non-adenylated fragment were, respectively, amplified. After heat denaturing and cooling on ice of the resultant PCR product, it is subjected to electrophoresis using an SSCP electrophoretic gel made of 6% polyacrylamide gel containing 10% glycerol. A 1×TBE buffer containing 10% of glycerol is used as an electrophoretic buffer.

Figure 13A:
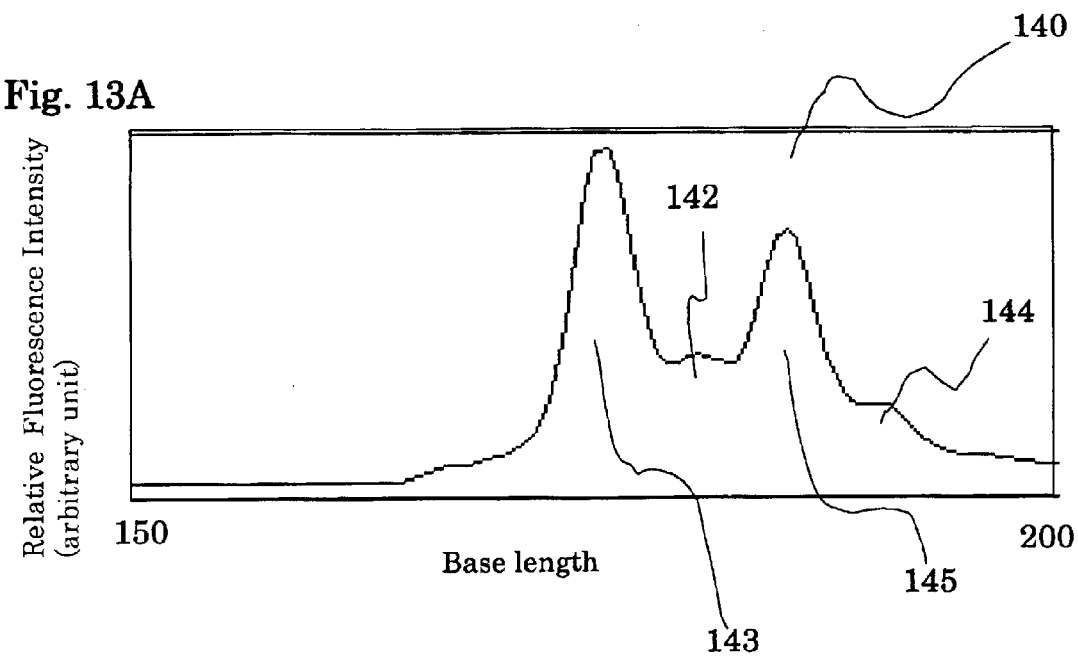
Figure 13B:
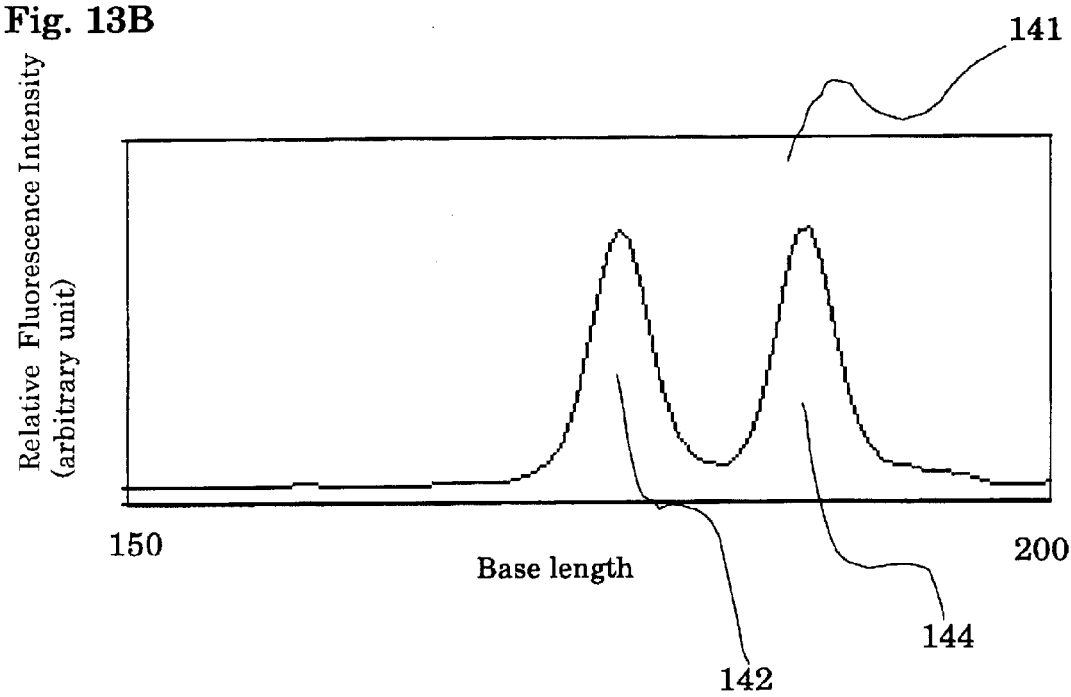

FIGS. 13A and 13B are, respectively, an instance of evaluating the influence of the adenylation on SSCP and correspond to FIGS. 2A to 2B. FIG. 13A shows an electropherogram 140 obtained as the results of analysis of the amplified product in PCR using an anchor sequence-free reverse primer, and FIG. 13B shows an electropherogram 141 obtained as the results of analysis of the amplified product in PCR using a reverse primer having an anchor sequence. In the electropherogram 140 of FIG. 13A, a peak 142 derived from an adenylated fragment amplified from paternal DNA, a peak 143 derived from a non-adenylated fragment amplified from paternal DNA, a peak 144 derived from an adenylated fragment amplified from a maternal DNA, and a peak 145 derived from a non-adenylated fragment amplified from maternal DNA are detected. In the electropherogram 140, the ratio between the non-adenylated fragment and the adenylated fragment is at 3:1, thus, the adenylated fragment being mixed at 10% or over. On the other hand, in the electropherogram 140 of FIG. 13B, a peak 142 derived from the adenylated fragment amplified from paternal DNA and a peak 144 derived from the adenylated fragment amplified from maternal DNA are detected. As will be seen from the figure, little non-adenylated fragment is detected in the electropherogram 141.

As will be appreciated from FIGS. 13A and 13B, when the adenylation is promoted by the reverse primer having an anchor sequence, the PCR product can be one wherein a non-adenylated fragment is removed from a mixture of a non-adenylated fragment and an adenylated fragment. As a result, diagnosis with SSCP can be made more accurately.

EXAMPLE 3

The method of the invention can be applicable to multiplex PCR. In the same manner as in Example 1, target DNA is subjected to PCR amplification by use of a fluorescence-labeled PCR forward primer and a reverse primer having an anchor sequence. In Example 1, the procedure is illustrated on the assumption that one target DNA is amplified through one reaction tube. In multiplex PCR, a plurality of target DNA's are simultaneously amplified by in reaction tube, and the resulting PCR products are electrophoretically separated and simultaneously detected. The anchor sequence may be one which should satisfy the requirement that the sequence is not complementary to target DNA, and can be design irrespective of the sequence of the target DNA, so that the same anchor sequence is usable against all the PCR reverse primers.

Figure 14A:
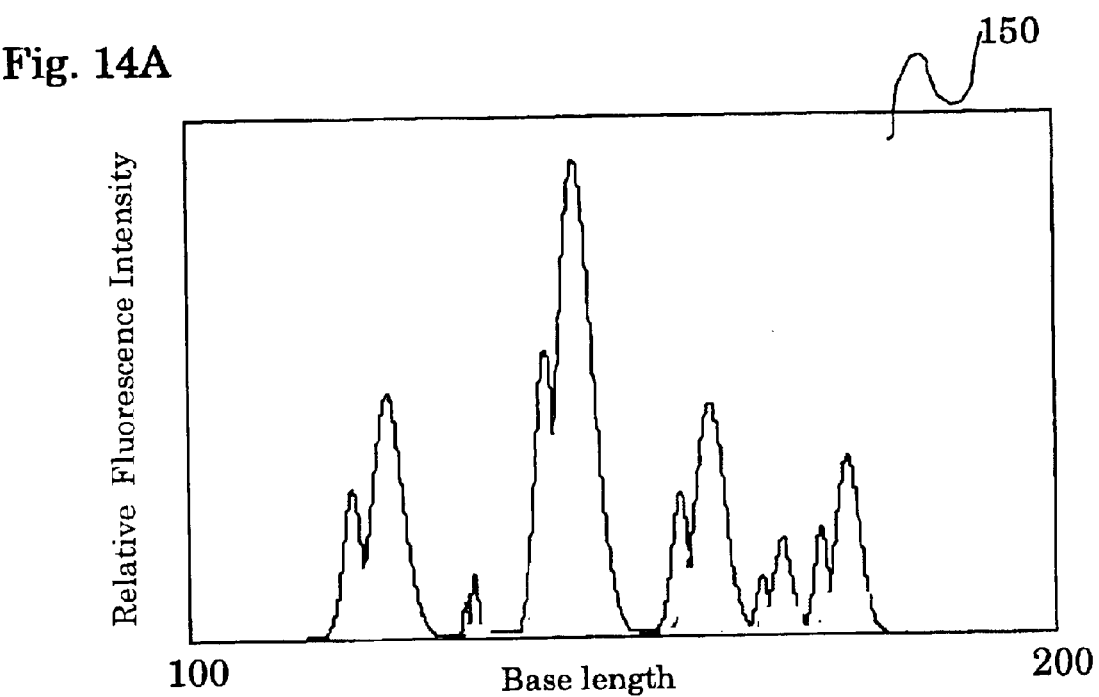
FIG. 14A is an electropherogram in case where a target DNA is subjected to PCR using a fluorescence-labeled PCR forward primer group and an anchor sequence-free PCR reverse primer group.
Figure 14B:
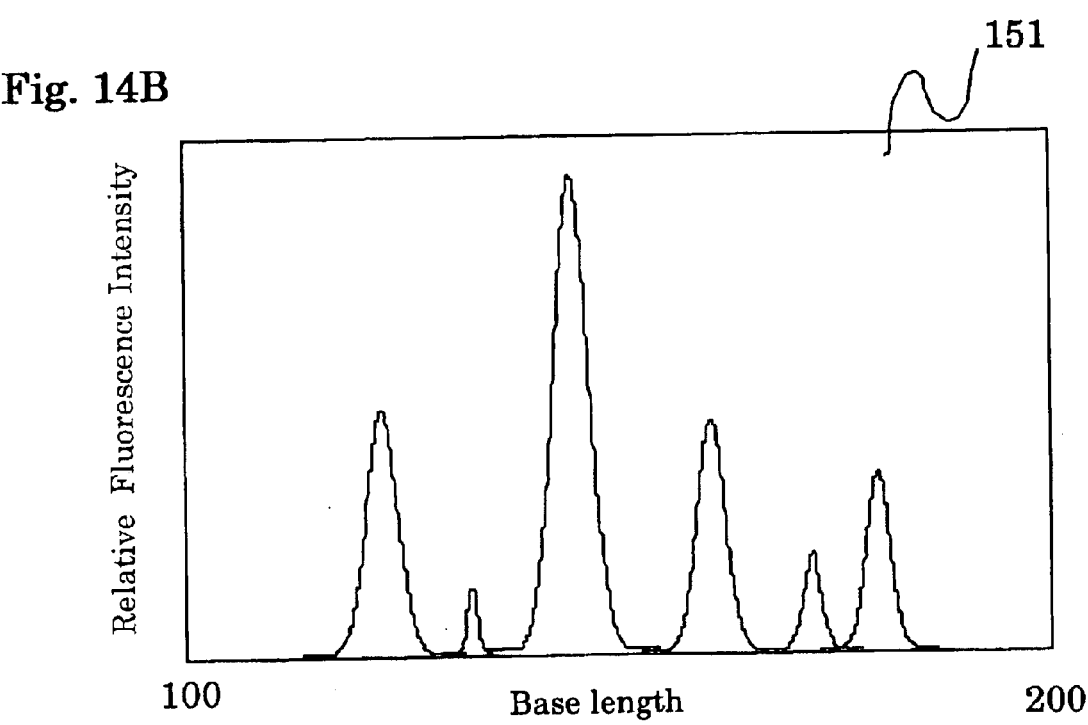
FIG. 14B is an electropherogram in case where a target DNA is subjected to PCR using a fluorescence-labeled PCR forward primer group and a reverse primer having an anchor sequence.

FIG. 14A is a view showing an electropherogram 150 of the case where target DNA is subjected to PCR by use of a group of fluorescence-labeled PCR forward primers and a group of anchor sequence-free PCR reverse primers and the resultant PCR products are electrophoretically analyzed. FIG. 14B is a view showing an electropherogram 151 of the case where target DNA is subjected to PCR by use of a group of fluorescence-labeled PCR forward primers and a group of reverse primer having an anchor sequence and the resultant PCR products are electrophoretically analyzed. As shown in FIG. 14A, where multiplex PCR is performed without use of an anchor sequence promoting the adenylation efficiency, the peaks of the electropherogram 150 are closed to one another and quantitative analyses thereof may be difficult in some cases. However, as shown in FIG. 14B, when multiplex PCR is performed by use of the PCR primers that, respectively, have an anchor sequence facilitating the adenylation efficiency, the peaks are kept more distant from one another as seen in the electropherogram 151. This enables one to carry out a high degree of multiplexing. In Example 3, because any peak derived from a non-adenylated fragment is not detected, a high degree of multiplexing becomes possible.

Example of a Software For Deciding an Anchor Sequence

At a stage of deciding a primer sequence by use of PCR, the use of a software capable of simply designing a base sequence of a PCR primer having an anchor sequence is beneficial.

Figure 15:
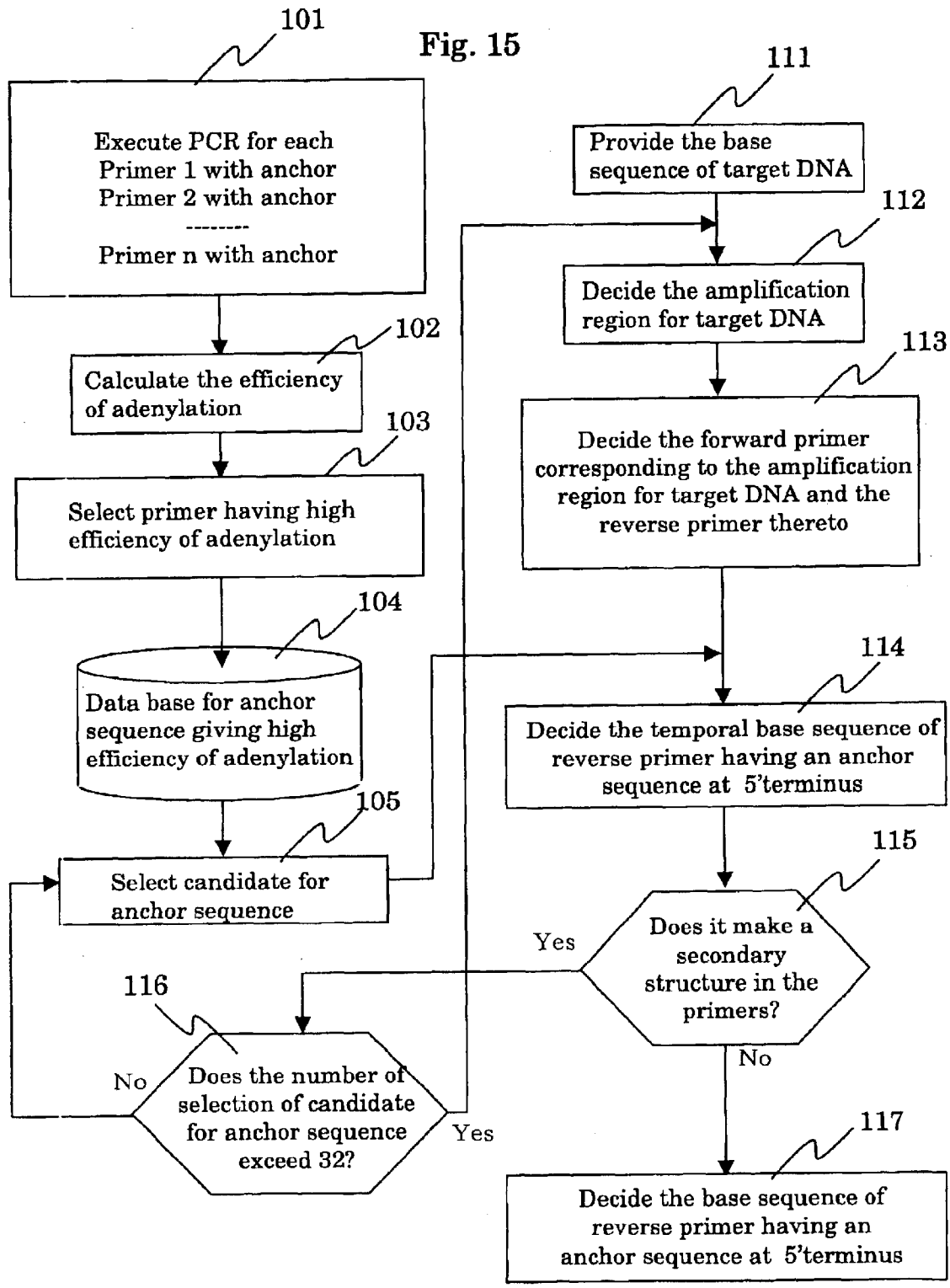
FIG. 15 is a flowchart showing an example of software for simply designing a base sequence of a PCR primer having an anchor sequence.

FIG. 15 shows an example of a flow chart of a soft ware designed therefor. In step 101, a PCR reverse primer with an anchor sequence to a PCR reverse primer n with an anchor sequence are each subjected to PCR in the same manner as illustrated with reference to FIGS. 3A–3D to 11. In step 102, the efficiency of adenylation is calculated from each of the products of PCR carried out in the step 101 with respect to the PCR reverse primers having the respective anchor sequences. In step 103, the efficiencies of adenylation are compared with one another from the results of the step 102 to judge and select a PCR reverse primer having an anchor sequence capable of giving a higher adenylation efficiency. In step 104, an anchor sequence capable of giving a high efficiency of adenylation is stored in a file from result of step 103. Attention should be paid here to the fact that in step 103, although a PCR reverse primer with an anchor sequence capable of giving a higher efficiency of adenylation is selected, this soft wafer is intended to select an anchor sequence for application to arbitrary target DNA and the anchor sequence alone is cut off from the PCR reverse primer having the selected anchor sequence and stored in the file.

Those steps up to the step 104 are a so-called preparatory stage of this soft ware, and the process of deciding a PCR primer for target DNA includes step 105 onward.

In step 111, a sequence of target DNA is introduced. In step 112, an amplification region of the target DNA is decided. In step 113, base sequences of a PCR forward primer and a PCR reverse primer, which, respectively, correspond to the sequences of amplification region of target DNA are so designed appropriate Tm value and not to form either an interprimer or intraprimer secondary structure. Next, in step 114, one of anchor sequences stored in the file prepared beforehand (i.e. a candidate for anchor sequence) is retrieved and joined at the 5' terminus of the PCR reverse primer designed in the step 113 to temporarily decide an anchor sequence-bearing PCR reverse primer. In step 115, it is evaluated whether or not the PCR reverse primer that is so designed as not to form a secondary structure has the secondary structure formed in the step 113 as a result of the addition of the anchor sequence. If a secondary structure or a dimer of the primer is formed, a candidate for another anchor sequence is selected and a PCR reverse primer having the selected anchor sequence is temporarily decided. If any secondary structure is not formed, the temporarily decided primer in the step 117 is decided as a reverse primer having an anchor sequence.

In the step 115, when anchor sequences are judged as ones that form a secondary structure 32 times or over, i.e. when the step 116 is judged as Yes, the procedure is returned to the step 112 wherein the amplification region of the target DNA is decided again, followed by repeating the above-stated procedure to decide a reverse primer having an anchor sequence-bearing PCR reverse primer. It will be noted that in this example, the anchor sequence is checked 16 times with respect to all the anchor sequences of two bases subsequent to GA at the 5' terminus and the anchor sequence is also checked 16 times with respect to all the anchor sequences of two bases subsequent to GG at the 5' terminus. If a secondary structure is formed in all of these checks, the procedure is returned to step 112.

As will be apparent from the above, if the software is used, an anchor sequence capable of giving a high efficiency of adenylation can be simply decided from among a plurality of anchor sequences. Additionally, an anchor sequence that gives a high efficiency of adenylation can be stored in a file, and can be selected as a candidate for an anchor sequence against a variety of primers. To check whether or not an anchor sequence-added primer has a secondary structure formed therein enables one to simply design a PCR primer having an anchor sequence and decide a base sequence. If information of a target DNA sequence and an approximate base length of an amplified product is obtained from a user, design service of a PCR primer having an anchor sequence is possible.

Others

In the above-stated examples, the addition of an anchor sequence to a PCR reverse primer on the assumption that a PCR forward primer is labeled with a fluorophore has been illustrated. Needless to say, the invention is also applicable to the case where a PCR reverse primer is subjected to fluorescence labeling. In this case, an anchor sequence is added merely to the 5' terminus of the PCR forward primer.

Moreover, an anchor sequence may be, respectively, attached to both a PCR forward primer and a PCR reverse primer.

In PCR of a target DNA sequence, anchor sequence-added primer enables adenylation at the terminus of a DNA fragment at a high efficiency, resulting in the analysis of high resolution.

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: forward DNA primer which is used in PCR and
      hybridizes with DNA fragment originated from yeast gene.

<400> SEQUENCE: 1
agaagagggc tccaatttct c                                              21

<210> SEQ ID NO 2
<211> LENGTH: 22
<212> TYPE: DNA
<213> ORGANISM: Artificial Sequence
<220> FEATURE:
<223> OTHER INFORMATION: base sequence of a part of reverse DNA primer
      which is used in PCR and the base sequence of a part of
      reverse DNA primer hybridizes with DNA fragment
      originated from yeast gene.

<400> SEQUENCE: 2
gtgagcaata cacaaaattg ta                                             22
```

Free text of a sequence table:

(1) Description of other related information relating to the sequence of sequence No. 1.
A forward primer for amplifying yeast gene (YGR281W)
(2) Description of other related information concerning the sequence of Sequence No. 2.
A sequence complementary to yeast gene (YGR281W) of a reverse primer for amplifying the yeast gene (YGR281W).

What is claimed is:

1. A method for determining a base sequence of a primer comprising:

carrying out a PCR by using four types of primers which respectively have a structure comprising a first sequence of a given base length complementary to one of single strands of a target DNA and a second sequence of a given base length provided adjacent to the side of 5' terminus of said first sequence and being non-complementary to the one of single strands of the target DNA;

analyzing results of amplified products obtained by the PCR;

requiring efficiencies of adenylation using results of the step of analyzing;

determining one out of the four types of primers as a sequence which is most likely to undergo adenylation, wherein each of the four types of primers have one base at 5' terminus of the second sequence, the one base being different among the four types of primers;

carrying out a second PCR by using another four types of primers which respectively have the one base at the 5' terminus of the second sequence of the sequence determined in the step of determining one out of the four types of primers, and have a second base located at a second site from the 5' terminus thereof and different among the another four types of primers;

analyzing second results of amplified products by the second PCR;

requiring efficiencies of adenylation using results of the step of analyzing the second results; and determining one out of the another four types of primers to be most likely to undergo adenylation.

2. A method for determining a base sequence of a primer comprising:

carrying out a PCR by using four types of primers which respectively have a structure comprising a first sequence of a given base length complementary to one of single strands of a target DNA and a second sequence of a given base length provided adjacent to the side of 5' terminus of said first sequence and being non-complementary to the one of single strands of the target DNA;

analyzing results of amplified products obtained by the PCR;

requiring efficiencies of adenylation using results of the step of analyzing;

determining one out of the four types of primers as a sequence which is most likely to undergo adenylation, wherein each of the four types of primers have one base at 5' terminus of the second sequence, the one base being different among the four types of primers;

carrying out a second PCR by using another four types of primers which respectively have the one base at the 5' terminus of the second sequence of the sequence determined in the step of determining one out of the four types of primers, and have a second base located at a second site from the 5' terminus thereof and different among the another four types of primers;

analyzing second results of amplified products by the second PCR;

requiring efficiencies of adenylation using results of the step of analyzing the second results;

determining one out of the another four types of primers to be most likely to undergo adenylation;

carrying out a third PCR by using other four types of primers which respectively have the one base at the 5' terminus of the second sequence of the sequence determined in the step of determining one out of the another four types of primers, and have a third base located at a third site from the 5' terminus thereof and different among the other four types of primers;

analyzing third results of amplified products obtained by the third PCR;

requiring efficiencies of adenylation using results of the step of analyzing the third results; and determining one out of the other four types of primers to be most likely to undergo adenylation.

* * * * *